March 23, 1948. DE ROSS KELLOGG Plant Pat. 793
PLUM TREE
Filed Dec. 13, 1946
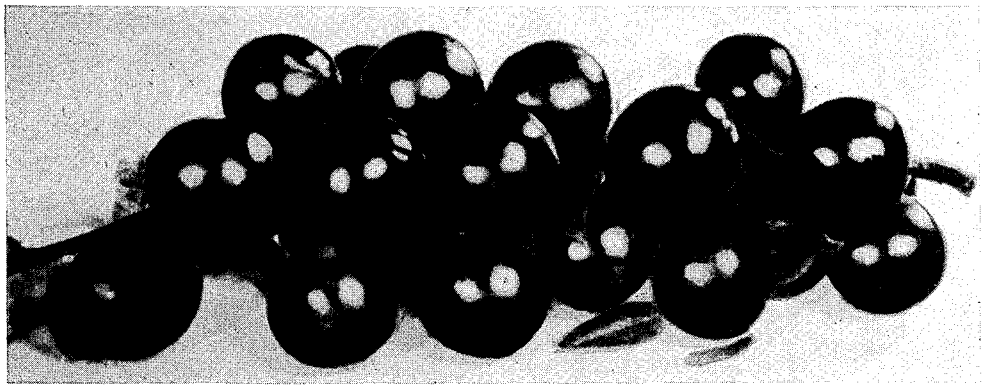
Inventor:
De Ross Kellogg
By: Robb & Robb
attorneys.

Patented Mar. 23, 1948

Plant Pat. 793

UNITED STATES PATENT OFFICE

793

PLUM TREE

De Ross Kellogg, Milford, Conn., assignor to Stark Bro's Nurseries and Orchards Company, Louisiana, Mo., a corporation of Missouri Application December 13, 1946, Serial No. 716,010

1 Claim. (Cl. 47—62)

The present discovery relates to a new and distinct variety of plum tree, originating as a chance seedling most nearly resembling in form and color of fruit and in tree characteristics the well-known Compass Cherry plum variety (unpatented.)

This new variety is distinguished from the Compass variety in that its fruit is approximately twice as large, is much superior in flavor. The tree also is hardy, vigorous in growth, a regular and heavy producer and both tree and fruit are disease resistant. By way of further distinction, when the Compass variety and this new variety are grown under comparable conditions, the fruit of the latter ripens approximately three days before the former.

These distinctive tree and fruit characteristics represent a marked improvement in plum trees, and said characteristics have been found to be established and fixed by asexual reproduction of the variety.

The drawing illustrates specimens of the fruit.

The following is a detailed description of the new variety, giving color designations according to the conventional dictionary definition of terminology as well as corresponding color terms according to Ridgway's Color Chart (observations were made near Louisiana, Missouri):

Dates first and last picking, July 13, 1945–July 20, 1945.

*Tree*

Medium size; vigorous; dense; spreading; vase-formed; hardy; very productive; regular bearer.

Trunk: Medium stocky; medium smooth.

Branches: Medium stocky; medium smooth; Dull Gray. Brownish red and glossy twigs (Ridgway, Plate XIV, Color 7', tone M). *Lenticels*—few; medium size.

Leaves: Length, 2¾''; width, 1⅛''. Medium size; oval; abruptly pointed; medium thick; smooth; Dark Green (Ridgway, Leaf Green, Plate XLI, Color 29''', tone M).

*Margin.*—Finely serrate.

*Petiole.*—Medium length.

*Glands.* — Medium size; reniform; free. Average number, 1.

Flowers: Dates first and full blossoms, March 22–March 28. Early compared with other varieties; medium size; white.

*Fruit*

Maturity when described—eating ripe.

Size: Uniform; large.

*Axial diameter.*—1⅜''.

*Transverse in suture plane.*—1½''.

*At right angles to suture plane.*—1½''.

Form: Uniform; symmetrical; globose.

*Suture.* — Distinct; shallow; extends from base to beyond but discontinues at apex.

*Ventral surface.*—Rounded.

*Cavity.*—Rounded; circular.

*Base.*—Rounded.

*Apex.*—Pistil point, apical.

*Stem.*—Slender; strong.

*Skin.*—Medium thick; medium tough; free. Tendency to break—none in wet season. Color—solid Red (Ridgway, Maroon, Plate I, Color 30, tone M).

Flesh:

*Color.*—Yellow (Ridgway, Olive Ocher, Plate XXX, Color 21''); next to skin, red (Ridgway, Oxblood Red, Plate I, Color 1, tone K).

*Amygdalin.*—Moderate; rich.

*Texture.*—Firm.

*Fibres.*—Few; fine.

*Ripens.*—Fairly even.

*Flavor.*—Subacid.

*Aroma.*—Distinct.

*Eating quality.*—Good.

Stone: Cling; adheres to flesh over entire surface.

*Fibres.*—Long.

*Length.*—$\frac{5}{16}$''; thickness, ¼''.

*Form.*—Oval; full.

*Base.*—Oblique; narrow; oval.

*Apex.*—Acute.

*Sides.*—Equal; smooth.

*Pits.*—Circular. Ventral edge—thin with wing throughout.

*Dorsal edge.*—Full with shallow groove toward base. Ridges on either side—continuous.

Use: Market; culinary; canning.

Keeping quality: Medium.

Resistance to: Insects and diseases—good.

Shipping quality: Good.

I claim:

A new and distinct variety of plum tree, having a similarity to the Compass Cherry plum variety but distinguished therefrom in respect to the large size of its fruit, superiority of the flavor and good disease resistance of the fruit, hardiness and vigor of growth of the tree, good disease resistance thereof, and regularity and productivity of its bearing, substantially as shown and described.

DE ROSS KELLOGG.